US00PP24831P3

(12) United States Plant Patent
Wheeler et al.

(10) Patent No.: US PP24,831 P3
(45) Date of Patent: Sep. 2, 2014

(54) BLUEBERRY PLANT NAMED "BB06-540FL-12"

(50) Latin Name: *Vaccinium corymbosum*
Varietal Denomination: BB06-540FL-12

(71) Applicant: Berry Blue, LLC, Grand Junction, MI (US)

(72) Inventors: Edmund J. Wheeler, Holland, MI (US); James F. Hancock, East Lansing, MI (US)

(73) Assignee: Berry Blue, LLC, Grand Juction, MI (US)

( * ) Notice: Subject to any disclaimer, the term of this patent is extended or adjusted under 35 U.S.C. 154(b) by 47 days.

(21) Appl. No.: 13/651,233

(22) Filed: Oct. 12, 2012

(65) Prior Publication Data

US 2014/0109266 P1 Apr. 17, 2014

(51) Int. Cl.
*A01H 5/00* (2006.01)

(52) U.S. Cl.
USPC ..... Plt./157

(58) Field of Classification Search
USPC ..... Plt./157
See application file for complete search history.

(56) References Cited

U.S. PATENT DOCUMENTS

| | | | |
|---|---|---|---|
| PP9,834 | P | 3/1997 | Lyrene |
| PP10,675 | P | 11/1998 | Lyrene |
| PP11,807 | P2 | 3/2001 | Lyrene |
| PP11,829 | P2 | 4/2001 | Lyrene |
| PP12,165 | P2 | 10/2001 | Lyrene |
| PP15,103 | P3 | 8/2004 | Hancock |
| PP15,146 | P3 | 9/2004 | Hancock |
| PP16,333 | P3 | 3/2006 | Lyrene |
| PP16,404 | P3 | 4/2006 | Lyrene |
| PP18,138 | P3 | 10/2007 | Nesmith |
| PP19,503 | P3 | 11/2008 | Lyrene |
| PP20,027 | P3 | 5/2009 | Lyrene |
| PP21,881 | P3 | 4/2011 | Patel |
| PP22,692 | P3 | 5/2012 | Nesmith |
| PP22,778 | P3 | 6/2012 | Wright et al. |

*Primary Examiner* — Annette Para
(74) *Attorney, Agent, or Firm* — Graybeal Jackson LLP

(57) ABSTRACT

A new and distinct cultivar of blueberry plant named 'BB06-540FL-12' as described and shown herein. 'BB06-540FL-12' is a new and distinct low chill tetraploid, as illustrated and described, Southern highbush blueberry (*Vaccinium*) variety based largely on *V. darrowii*. It is a productive, very early season ripening variety with high quality fresh market characteristics. It is intended for areas which successfully grow lower chill Southern highbush varieties. 'BB06-540FL-12' provides well-exposed fruit, an upright bush with a small crown, concentrated ripening, firm fruit and easy detachment. 'BB06-540FL-12' has an attractive blue color with medium amount of bloom, which is modestly maintained during handling. The flavor is very good with a balance of high sweetness levels and medium acidity. Berries have a crunchy and juicy texture with medium storage ability of 2 to 3 weeks.

4 Drawing Sheets

BACKGROUND AND SUMMARY

Blueberries are a well-known fruit enjoyed by many throughout the world. One example of an existing, patented blueberry variety is Star, U.S. Plant Pat. No.10,675. Another example of an existing, patented blueberry variety is Sweetcrisp, U.S. Plant Pat. No. 20,027.

Compared to Star, the maturity of the present cultivar, 'BB06-540FL-12', is 21-25 days earlier. The bush shape is very erect as compared to Star. In addition, in BB06-540FL-12 new fruiting wood, petioles are light pink colored early in the season. 'BB06-540FL-12' produces fruit that is slightly larger and more round in shape than Star.

Compared to Sweetcrisp, the maturity of 'BB06-540FL-12' is earlier by 18-21 days. 'BB06-540FL-12' has a slightly smaller and less firm berry, a more upright bush shape, and a more concentrated harvest.

The present cultivar, 'BB06-540FL-12', provides one or more advantages compared to these and/or other blueberry varieties, such as very early season ripening variety with high quality fresh market characteristics.

BRIEF DESCRIPTION OF THE PHOTOGRAPHS

Figure 1:
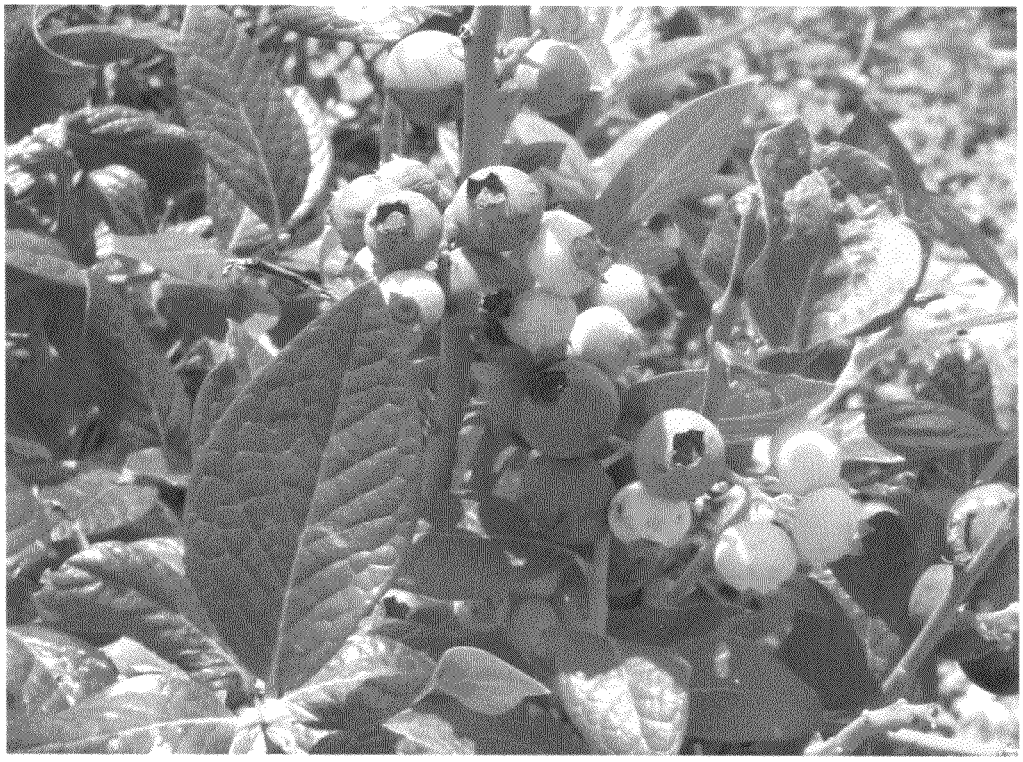
FIG. 1 is a photograph taken in April 2012 of the Blueberry cultivar 'BB06-540FL-12', showing mature leaves, unripe and ripe fruit with fruit color, size, shape, fruit cluster density, and calyx features.
Figure 2:
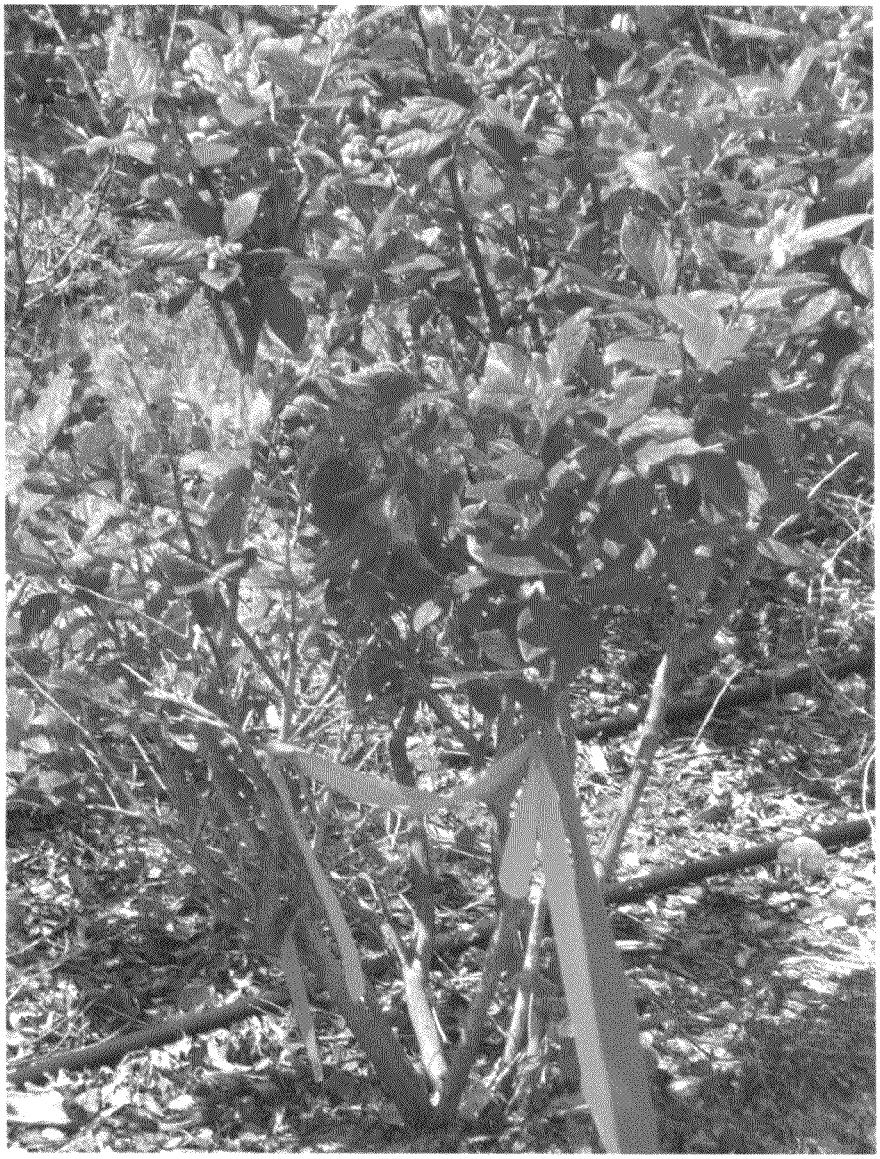
FIG. 2 is a photograph taken in April 2012 of the Blueberry cultivar 'BB06-540FL-12', showing a 6 year old bush with ripened fruit, as well as bush shape, cane growth, leaf shape and color, and glossy leaves.
Figure 3:
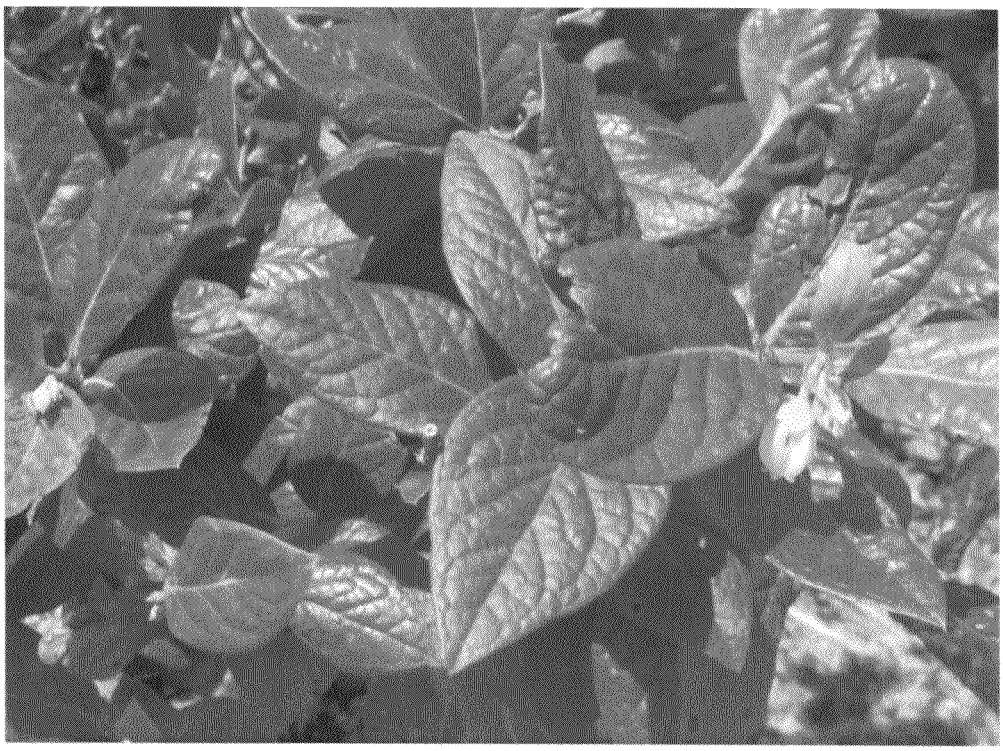
Figure 4:
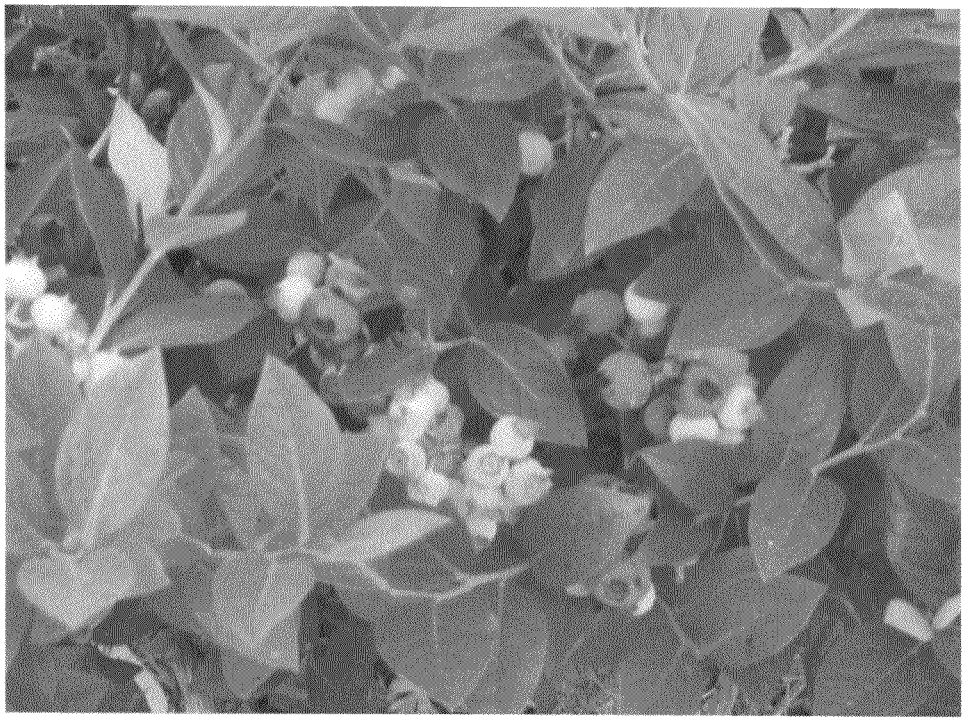

FIG. 3 is a photograph taken in April-May 2012 of the Blueberry cultivar 'BB06-540FL-12', showing mature leaf shape, color and venation, opened flower and flower buds, and glossy, thick leaves FIG. 4 is a photograph taken in April 2012 of the Blueberry cultivar 'BB06-540FL-12', showing ripe and unripe fruit, leaf shape, and pinkish coloration of stems, petioles, peduncles and leaf venation during cool temperatures.

DETAILED DESCRIPTION

Note: statements of characteristics herein represent exemplary observations of the cultivar herein and will vary depending on time of year, location, annual weather, etc. Where dimensions, sizes, colors, and other characteristics are given, it is to be understood that such characteristics are approximations and averages. The descriptions reported herein are largely from specimen plants grown near Interlachen, Fla. Data were obtained on plants that were 6 years old.

Cultivar name: 'BB06-540FL-12'.

Classification:

*Family*.—Ericaceae.

*Botanical name*.—*Vaccinium corymbosum*.

*Common name*.—Blueberry.

Parentage:

*Female parent*.—Name: Sapphire (parents unknown). U.S. Plant Pat. No. 11,829. Compared to Sapphire, 'BB06-540FL-12' has a more round berry shape, a lighter blue color of ripened berries, and matures 2 weeks earlier. 'BB06-540FL-12' also has a more erect bush shape, and leaves and flowers of 'BB06-540FL-12' appear to have better cold tolerance.

*Male parent*.—Name: Snowchaser (FL95-57 unpatented×FL89-119 unpatented). U.S. Plant Pat. No. 19,503. Compared to Snowchaser, 'BB06-540FL-12' has a more upright bush shape, and leafs at the time of flowering. 'BB06-540FL-12' also has a slightly larger berry that maintains uniformity of size through harvest, and the leaves, flowers, and fruit of 'BB06-540FL-12' appear to have better frost tolerance.

'BB06-540FL-12' was first asexually propagated by softwood cuttings. For example, softwood cuttings of this variety were first taken and rooted in 2008 in Grand Junction, Mich., and have been propagated several times since in succeeding years. All propagated plants have retained the original characteristics. Softwood cuttings and microshoots from tissue culture root readily, but using young shoots for cuttings results in higher rooting percentages.

Field observations were made in Spring 2012 on a 6-year old individual plant located in a seedling plot near Interlachen, Fla. Laboratory analysis of fruit characteristics were done in Grand Junction, Mich.

General comments: 'BB06-540FL-12' is a new and distinct low chill tetraploid, as illustrated and described, Southern highbush blueberry (*Vaccinium*) variety based largely on *V. darrowii*. It is a productive, very early season ripening variety with high quality fresh market characteristics. It is intended for areas which successfully grow lower chill Southern highbush varieties. 'BB06-540FL-12' provides well-exposed fruit, an upright bush with a small crown, concentrated ripening, firm fruit and easy detachment. This variety is suitable for mechanical harvesting. Winter chilling requirements for successful flowering and leafing are approximately 200 hours (<7° C.). Plants of 'BB06-540FL-12' are upright with growth of primary canes and laterals. Flowering and leafing are synchronous, and it can be evergreen in warmer climates. This variety does display a tendency to produce a small percentage of fall and early winter blooms. Flowering is early (northern Florida) and may often require frost protection for successful pollination. Plant vigor is good and doesn't appear to be overly susceptible to foliar and soil diseases if normal horticultural practices are followed. Its berries are well exposed, large in size, nearly round in shape, with a small dry picking scar. It has an attractive blue color with medium amount of bloom, which is modestly maintained during handling. The flavor is very good with a balance of high sweetness levels and medium acidity. Berries have a crunchy and juicy texture with medium storage ability of 2 to 3 weeks. Thus, 'BB06-540FL-12' provides a very early maturing, very glossy thick leaves, some higher cold tolerance, roundish firm berry with excellent eating qualities, very sweet, and flavorful fruit.

References to color refer to The Pantone Book of Color, Eisemann and Herbert, Harry N. Abrams, Inc. Publishers, New York, ISBN 0-8109-3711-5, 1990.

The Device used to take color readings was a SpectraMagic NX Model CR410, Konica Minolta, Japan.

Morphological characteristics reference: Plant Systematics, Jones and Luchsinger, 2 Ed., McGraw Hill, N.Y., ISBN 0-07-032796-3, 1986.

Firmness readings—BioWorks FirmTec2, Wamena, Kans.

Average size information:

*General description*.—Medium large bush, upright, 6-year plant 105 cm height, 70 cm width, height/width ratio 1.5:1.

*Growth*.—Very good.

*Productivity*.—Good.

*Cold hardiness*.—Leaf and flower buds −5° C., open flowers and fruit −2° C.

Specific features of the variety:

Plant:

*Growth habit*.—Upright.

*Plant width*.—70 cm at mid-bush.

*Plant height*.—105 cm.

*Spread*.—Canopy 75 cm.

*Productivity*.—4-5 lbs per mature bush.

*Cold hardiness/tolerance*.—Leaf and flower beds −5° C., flowers and fruit −2° C.

*Chilling requirement*.—Approximately 200 hours below 7° C.

*Canes*.—Modestly branched, average 6 canes/bush, 22-30 cm length, medium number of laterals. Mature cane color: — Pantone Stucco 16-1412, texture medium rough.

*Fruiting wood*.—Smooth, immature winter color — Pantone Mineral Red 17-1537, immature summer color — Pantone Green Moss 17-0636; Internode length range 18-20 mm; width 5 mm.

*Surface texture of new wood*.—Smooth, mature canes — circular, width 10-13 mm.

*Time of beginning of leaf bud burst* (*include location*(*s*)) .—January 25 (Interlachen, Fla.).

*Time of beginning of flowering* (*include location*(*s*)).—January 15 (Interlachen, Fla.).

*Time of fruit ripening* (*include location*(*s*)).—April 1 (Interlachen, Fla.).

*Disease resistance/susceptibility*.—None claimed.

Foliage:

*Leaf color*.—Upper — Pantone Avocado 18-0430, Lower — Pantone Loden Green 18-0422.

*Leaf arrangement*.—Alternate, shape — Elliptic.

*Leaf margins*.—Entire.

*Leaf venation*.—Pinnate.

*Leaf apices*.—Acute.

*Leaf bases*.—Cuneate.

*Vein and petiole colouration*.—Cool season — Pantone Candy Pick 14-1911; warm season — Pantone Beechnut 14-0425.

*Petiole length*.—4 mm.

*Leaf dimensions*.—Overall shape: 62 mm-74 mm, average 67 mm. Width: 33 mm-40 mm, average 37 mm.

*Leaf margins*.—Entire, no pubescence or nectaries.

*Leaf surface*.—Smooth upper and lower, no pubescence.

Flower:

*Flower shape*.—Elongate urceolate.

*Flower bud number*.—Medium high.

*Flowers per cluster*.—6-9 average 7.

*Flower fragrance*.—Lightly sweet and floral.

*Corolla color*.—Cool temperatures — Pantone Aurora Pink 15-2217; warm — Pantone Ice 11-4803.

*Corolla length*.—7-9 mm, average 8 mm.

*Corolla aperture width*.—3 mm.

*Flower peduncle*.—Length 10 mm.

*Color*.—Pantone Cardinal 18-1643.

*Flower pedicel*.—3 mm.

*Color*.—Pantone Cardinal 18-1643.

*Calyx* (*with sepals*).—2 mm.

*Color*.—Pantone Olive Green 17-0929.

*Stamen*.—Length: 7 mm.

*Number per flower*.—10.

*Filament color*.—Pantone Rawhide 18-1137.

*Style*.—7-9 mm, average 8 mm.

*Color*.—Pantone Hemp 14-0721.

*Pistil*.—8 mm.

*Ovary color*.—NA.

*Anther*.—Length: 3 mm.

*Number*.—10/flower.

*Color*.—Pantone Rawhide 18-1137.

*Pollen*.—Abundance: Medium. Color: Pantone Cream Gold 13-0739.

Fruit:

*Date of* 50% *maturity*.—April 3 (Interlachen, Fla.).

*Yield*.—4-5 lbs/bush.

*Berry color*.—With wax: Pantone Blue Ice 17-3922, SpectraMagic (L,a,b) 40. 50, 0.97, −2.48. With wax removed: Deep Cobalt 19-3935. Berry flesh color: Pantone Frozen Dew 13-0513. Berry surface wax abundance: Medium, moderately persistent.

*Calyx*.—Width — 7 mm; depth — 1 mm; shape — 5 lobed with pronounced ridges.

*Berry weight*.—1.9 grams/berry.

*Berry size diameter*.—17 mm width, 14 mm height, Aspect (H/W) — 0.8.

*Berry shape*.—Oblate.

*Fruit stem scar*.—Small, dry, 2 mm.

*Cluster density*.—Loose.

*Detachment force*.—Medium easy.

*Self-fruitfulness*.—Poor, will need cross pollination for maximum yield and size.

*Berry firmness*.—Medium firm, FirmTec 2 score — 210 g/mm$^2$.

*Berry sweetness*.—Medium high, Brix °12.3.

*Berry acidity*.—Medium low, TA — 0.21 (titratable acidity).

*Berry flavor and texture*.—Very good with balanced sweet flavor, crunchy and juicy.

*Suitability for mechanical harvesting*.—Good potential; bush shape, small crown, berry firmness, loose fruit cluster, and easy detachment are desirable characteristics for mechanical harvesting.

Seed:

*Seed abundance in fruit*.—Medium (10-12 seeds/fruit).

*Seed color*.—Pantone Baked Clay 18-1441.

*Seed dry weight*.—NA.

*Seed size*.—Medium, 1-1.5 mm/seed.

Possible typical market uses: Fresh market, processing into jams, puree, yogurt.

Storage quality: Medium, 2-3 weeks in refrigerated storage. In addition, the coloration of new stems, petioles, venation, especially if weather is cool, is a distinctive pinkish color.

What is claimed is:

1. A new and distinct cultivar of Blueberry plant named 'BB06-540FL-12' as described and shown herein.

* * * * *